(12) United States Patent
Bowling et al.

(10) Patent No.: US 10,502,749 B1
(45) Date of Patent: Dec. 10, 2019

(54) METHOD FOR PATIENT STRATIFICATION AND DRUG EFFICACY MONITORING

(71) Applicant: New York University, New York, NY (US)

(72) Inventors: Heather L. Bowling, Jersey City, NJ (US); Aditi Bhattacharya, Bangalore (IN); Eric Klann, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/617,820

(22) Filed: Jun. 8, 2017

Related U.S. Application Data

(60) Provisional application No. 62/347,413, filed on Jun. 8, 2016.

(51) Int. Cl.
| | |
|---|---|
| *C07K 16/40* | (2006.01) |
| *G01N 33/68* | (2006.01) |
| *A61K 31/506* | (2006.01) |
| *C12Q 1/34* | (2006.01) |
| *G01N 33/573* | (2006.01) |

(52) U.S. Cl.
CPC ....... *G01N 33/6893* (2013.01); *A61K 31/506* (2013.01); *C07K 16/40* (2013.01); *C12Q 1/34* (2013.01); *C12Y 306/05002* (2013.01); *G01N 33/573* (2013.01); *G01N 2333/914* (2013.01); *G01N 2800/52* (2013.01)

(58) Field of Classification Search
CPC .... A61K 2300/00; C12N 9/001; C12N 15/85; C12N 9/2402; C07K 16/18; C07K 16/28; C07K 16/40
See application file for complete search history.

(56) References Cited

U.S. PATENT DOCUMENTS

2004/0101874 A1* 5/2004 Ghosh ................ G01N 33/5079
435/6.12

OTHER PUBLICATIONS

Full Moon Biosystems, "Signaling Explorer Antibody" microarray (SET100) website, published [online] Oct. 6, 2014. Retrieved at : <https://web.archive.org/web/2014/https://www.fullmoonbio.com/product/signaling-explorer-antibody-array/> Retrieved on: Oct. 24, 2018. and attached "Antibody List" (Year: 2014).*

* cited by examiner

*Primary Examiner* — Kimberly Ballard
*Assistant Examiner* — Stacey N MacFarlane
(74) *Attorney, Agent, or Firm* — Hodgson Russ LLP

(57) ABSTRACT

Identified are markers whose de novo synthesis or levels in blood provide are correlative information on the status of pathology, regardless of whether or not they correlate with the status in the relevant organ. The de novo synthesis or levels in blood can be used for patient stratification and monitoring the efficacy of treatment of diseases, such as fragile X syndrome.

4 Claims, 12 Drawing Sheets

Table 2. Summary of biomarker candidates in blood

| | Predicted basal (FXS/WT) | Predicted DHPG | Detected in blood? |
|---|---|---|---|
| mGluR5 | Up | Up | Y |
| NMDAR2B | Down | Not consistent | Y |
| SynGap | Up | Up FXS | Pending |
| Cofilin | Down | Not consistent | N |
| TrkB | Not consistent | Down FXS | Y |
| Eif2alpha | Not consistent | Down FXS WT | Y |
| Aco2 | Up | Not consistent | Y |
| Dynamin-I | Down | Down WT | Y |
| HRas/Ras | Not detected | Up FXS (WT not detected) | Y |
| Clathrin light chain | Up | Not consistent | Faint |
| PAK1 | Not consistent | Up FXS | Y |
| Hexokinase I | Down | UP FXS WT | Y |
| Acyl-coA binding protein (DBI) | Up | Up FXS | N |
| Transferrin Receptor | - | - | Y |
| Biotin | - | - | Y |
| Vimentin | Not consistent | Down FXS | Pending |

Figure 5

- Generate candidate list from de novo protein synthesis analysis (e.g., mass spectrometry)
- Examine candidates most related to available information (e.g., number of relevant references, cellular processes associated with the disorder, GO analyses)
- Select top desired number of markers (e.g., 50)
- Determine expression of the protein (protein and/or RNA level) level (independently or from publicly available databases and literature)
- Select candidates with available detecting molecules such as antibodies, preferably with proven track records in humans and mice (e.g., ELISA and Western blot) ~10-15 candidates
- Test antibodies in plasma, serum, whole blood
- Test if protein is present at detectable levels in any fraction.
- Identify the best fraction for detection
- Run patient samples (e.g., ELISA or Western) using optimized preparation and compare to loading control (e.g., TFN Receptor)
- Perform blinded analysis (second party)
- Compare control vs patients – look for groups that have no overlap in the dot plots and groups where some of the dots overlap and others do not
- Record the dots that do not overlap vs those that do with control
- Compare the list to known clinical presentation – genetic profile, age, secondary pharmaceutical agents
- Examine several markers and examine individual patient performance across candidates
- Establish and track patient database
- Identify patient "type" based on profile with candidates and track through clinical trials

Figure 9

- Generate candidate list from de novo protein synthesis mass spectrometry
- Examine candidates most related to available information (e.g., number of references in literature, cellular processes associated with the disorder; GO analyses)
- Select top desired number of markers (such as 50)
- Examine therapeutic mechanism of action and select known/likely targets based on target of therapeutic
- Choose 10-15 targets based on relationship to mechanism of action of drug, relationship to disease and antibody performance
- Treat animals with paradigm supported by literature or one that improves behavior – then test for changes in abundance of candidates in the relevant tissue (e.g. cortex)
- Quantify and analyze (blinded) and establish which candidates respond to treatment
- Using treated blood samples from patients (crossover studies, placebo vs treated, untreated then treated in same patients) test for candidates
- Quantify and analyze (blinded study)
- Compare changes in markers to performance on behavioral and physiological exams (and cross reference with the patient profile established using above patient stratification protocol)
- Make patient stratification x protein candidate performance report in response to drug
- Correlate patient stratification status groups with drug performance
- Identify which patients respond to the drug based on their profiles.

Figure 10

METHOD FOR PATIENT STRATIFICATION AND DRUG EFFICACY MONITORING

CROSS-REFERENCE TO RELATED APPLICATIONS

This application claims priority to U.S. Provisional patent application No. 62/347,413, filed Jun. 8, 2016, the disclosure of which is incorporated herein by reference.

STATEMENT REGARDING FEDERALLY SPONSORED RESEARCH

This invention was made with government support under contract nos. NS034007, NS047384 and HD082013, awarded by the National Institutes of Health. The government has certain rights in the invention.

BACKGROUND OF THE DISCLOSURE

Altered expression of specific proteins (or protein concentration) in relevant organs or tissues has been implicated in many diseased states. However, a reliable and easy measurement of such altered protein synthesis is not available or feasible for all disease indications. Studies on RNA changes are not always correlative with protein expression, and DNA at best is a static measure of heredity and does not reflect the dynamics of disease progression. The concentration of any protein is achieved by a balance of its synthesis and degradation rates. In diseases that have a clear basis in dysfunctional protein synthesis (like Fragile X syndrome), it is important to know which proteins are synthesized and persist aberrantly in cells. Monitoring a collection of proteins expression patterns simultaneously can offer larger dynamic range or power of correlation to patient phenotypes and symptoms.

SUMMARY OF THE DISCLOSURE

The present disclosure provides methods and kits for stratification of patients based on markers associated with specific indications that are detectable in blood and that are informative of status of the indication. The present disclosure also provides methods for identification of such markers that can be measured in easily accessible peripheral tissue, such as blood, and can be used an indicators of efficacy of treatment.

Understanding which proteins have altered concentration and get modified at the de novo expression level, and identifying globally altered protein candidates in the body for disease conditions like fragile X syndrome, represents a unique platform for patient stratification and efficacy measurement biomarkers. The present disclosure provides a method for identification of protein markers in blood that can be used as surrogates for the status of these proteins in relevant organs or tissues, thereby providing predictive correlates of the pathology.

The method comprises identifying a set of proteins from large scale screen data (such as proteomics and transcriptomics) modelling a disease condition or indication and identifying the proteins whose de novo synthesis or level in one or more relevant tissues or organs is correlated with pathology. The method then refines these potential candidate proteins to those that can be detected in blood, and then further filtering the candidate list to those whose concentration in blood is correlative of the status of the protein in relevant tissues or organs. In an embodiment, the method further provides identification of those proteins whose de novo synthesis in blood or levels are correlative with efficacy of treatment.

Once protein markers are identified whose de novo synthesis or concentration (also referred to herein as "level") is correlative of the status in relevant tissues or organs, blood samples from diseased individuals and appropriately matched controls can be examined to determine the levels of the identified proteins to provide an indication the status of the pathology. Blood samples can also be examined over a period of time, (such as over a treatment period) to provide an indication of the progression of the pathology or efficacy of the treatment.

By the method of this disclosure, one or more protein markers can be identified which are detectable in blood and which are correlative with the status of the proteins in relevant organs or tissues. These protein markers in blood can be used to stratify patients and measure treatment efficacy. For example, a panel of markers comprising two or more protein markers can be used to 1) differentiate and stratify patient populations based on changes in expression of panel members to help identify subgroups within the patient populations that may respond differently to treatment or have a different cluster of symptoms, and 2) use the panel to track treatment efficacy over time.

In one embodiment, this disclosure provides protein markers that can be used for stratification and treatment efficacy measurements in Fragile X syndrome (FXS). These markers may be measured in the whole blood, plasma or serum. In one embodiment, the markers may be Grin2b (Glutamate ionotropic receptor NMDA type subunit 2B), Ras (HRAS, NRAS and KRAS), mGluR5 (Metabotropic glutamate receptor 5), hexokinase, ACO2 (Aconitase 2), eIF2a (Eukaryotic translation initiation factor 2a), PAK1, Syngap (Synaptic Ras GTPase-activating protein 1), DBI (Acyl-CoA-binding protein), or combinations thereof.

The present disclosure also provides a method for stratification of patients afflicted with FXS into subpopulations that show different de novo synthesis or levels of certain markers in the blood compared to controls. The subpopulations can be matched to optimal treatment regimens and outcomes. Once such reference information is generated, a test patient can be evaluated for the markers and designated to a subpopulation. The individual can then be treated with the treatment regimen that is most suitable for that subpopulation.

The present disclosure also provides a method of personalized treatment of an individual afflicted with FXS comprising subjecting an FXS individual to a treatment, measuring the de novo synthesis in blood or levels in blood or a fraction thereof, of one or more markers identified herein, and based on the change in the synthesis or level of the marker(s), determining, at desired times, if the treatment is providing ameliorating effects with respect to FXS. De novo synthesis or the concentration in blood may be carried out for one or more of the following: Grin2b, Ras, mGluR5, hexokinase, ACO2, eIF2a, PAK1, Syngap, DBI. If the treatment if found to be effective, it may be continued.

BRIEF DESCRIPTION OF THE FIGURES

FIG. 5. Table 2 Summary of biomarker candidates selected.

FIG. 9. Illustrative example of method for identifying blood markers correlative of diseased conditions.

FIG. 10. Illustrative example of method for identifying blood markers that are indicative of efficacy of treatment.

DETAILED DESCRIPTION OF THE DISCLOSURE

The present disclosure provides methods pertaining to identifying protein markers in blood (or other biological fluids) which proteins or related isoforms are detected to be abnormal in relevant organs or tissue, and provide an indication of the status of the pathological condition. The present disclosure also provides a method for stratification of patients into subpopulations based on de novo synthesis in blood or concentration in blood of protein markers that are identified as being correlative with the status of a pathological condition in the relevant tissue. The disclosure further provides a method of treatment of an individual by monitoring the efficacy of the treatment by evaluating the de novo protein synthesis or concentration of specific markers in blood.

Any reference in this disclosure to determination of de novo synthesis of a marker in blood or determination of level of a marker in blood is equally applicable to and is a disclosure of determination of de novo synthesis and levels in plasma, serum or a fraction prepared from any of blood, plasma or serum.

Figure 1:
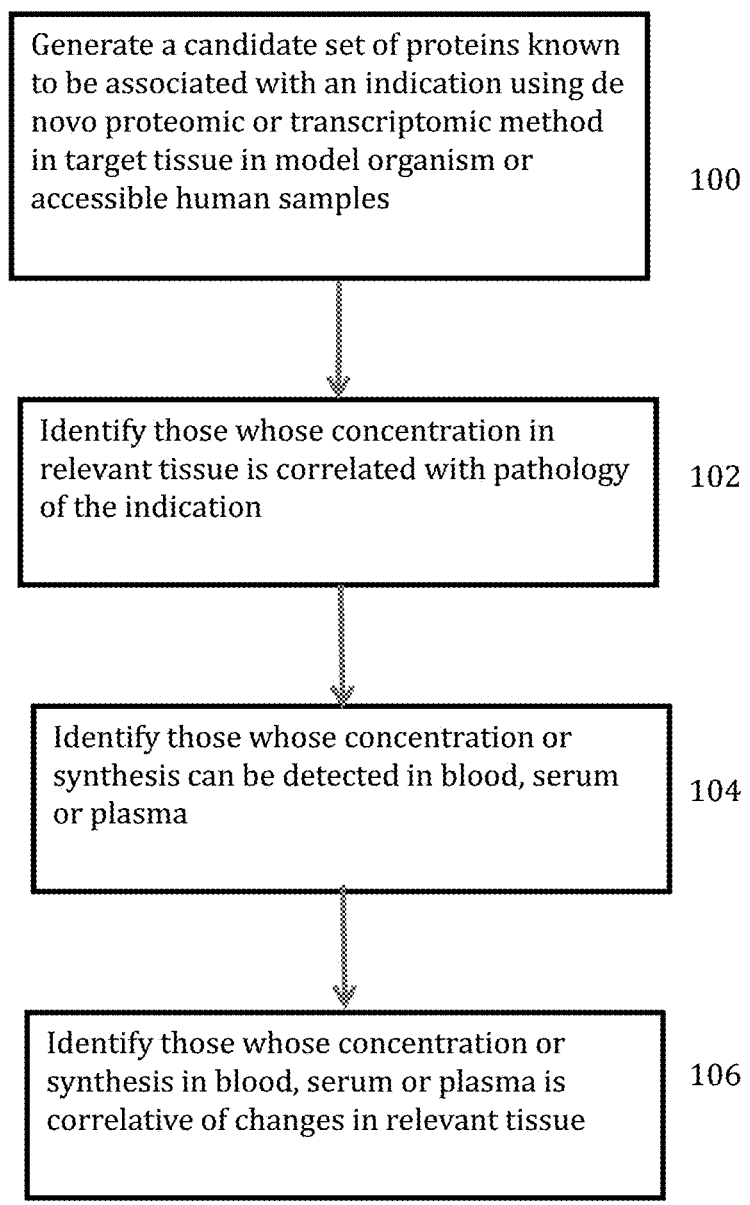
FIG. 1. Flow chart representing a method for identifying proteins whose status in blood is correlative with their status in relevant organs or tissues.

A method of the present disclosure comprises generating a set of candidate proteins known to be associated with an indication or pathology (such as by proteomic screen), identifying proteins whose concentration in relevant organs or tissues is correlated with pathology, identifying proteins which can be detected in blood or fractions or portions thereof, and identifying proteins in blood or fractions or portions thereof that are correlative with changes in the same proteins in relevant organs or tissues for the particular indication or pathology (FIG. 1). The terms concentration and level are used interchangeably in this disclosure.

The methods described herein are applicable for any indication, which could be a chronic or acute altered state (such as caused by interventional approaches), a chronic or acute pathological condition, or a chronic or acute physiological condition.

Referring to FIG. 1, in Step 100, the set of candidate proteins in relevant organs or tissues can be generated by proteomic or transcriptomic assays. This can provide a pattern of protein expression in the tissue. Alternatively or additionally, information can be gleaned from literature or other techniques (such as proteomics, transcriptomics and metabolomics) to assist in obtaining a first candidate protein set. A proteomic screen is useful because multiple candidates can be identified based on relevance to the pathology at the same level as protein candidates. These can then be systematically tested in other tissues based on their relevance to known disruptions at the molecular level and the pathology of the disease. If desired, the expression levels of such proteins (both at the transcription and translation level) can be verified in the relevant tissue or organ.

In Step 102, candidate proteins can be identified whose concentration in relevant tissue or organ is correlative with a pathology or indication. This can be because of changes in the proteins' synthesis rates or because of altered accumulation rates. Once a potential list of candidates is found, their levels can be determined in relevant tissue or organ samples obtained from animal model or samples from humans who are afflicted with the particular pathology or indication. If the samples are human samples, they can be obtained by biopsies. Animal models can also be used to obtain relevant tissue or organ samples.

In Step 104, proteins which can be detected in blood or a fraction thereof (plasma, serum or subpopulation of cells) are identified. In this step all the blood fractions or cellular subpopulations can be evaluated to determine the optimal fraction for detection of the marker.

In Step 106, proteins whose concentration in blood or a fraction thereof is correlative of changes in relevant tissue or organ are identified. This can be done on patient samples that may be available or may be done by prospective studies.

De novo protein synthesis can be used as a measure of the protein in a tissue, or blood (or any fraction). For measuring de novo protein synthesis in relevant tissues or organs, the cells of the tissue or organ are contacted with non-natural amino acid comprising a first reactive moiety under conditions such that the non-natural amino acid is incorporated into proteins that are newly synthesized in the cells. The first reactive moiety can then be used to detectably label proteins that incorporate the non-natural amino acid residue. This can be done by contacting with a second reactive moiety on a detectable reagent. The detectable reagent may comprises a functional moiety such as a fluorescent moiety, an affinity moiety etc., which can be detected. Detection of the functional moiety then is indicative of newly synthesized proteins. This technique is generally known as the Bioorthogonal Non-canonical amino acid tagging (BONCAT). This assay can be performed on tissues or organ samples using commercially available kits (such as Click-iT Protein reaction buffer kit and biotin-alkyne from Invitrogen). For measuring de novo protein synthesis in blood, the lysis buffer (used after incubation with a detectable, non-natural amino acid) should contain EDTA (or other divalent ion chelators) and then the samples are be dialyzed or processed to remove EDTA and other interfering substances (such as in spin columns) prior to carrying out cycloaddition reactions for detection of the non-natural amino acid.

As an example, proteins that are altered during treatment of an indication were identified for FXS. Two proteomic methods BONCAT and SILAC (Stable Isotope Labeling of Amino Acids in Culture/circuits) were used to label de novo protein synthesis in the mature adult mouse hippocampus providing candidate proteins relevant for FXS. Steady state protein synthesis was compared between FXS mice and their WT littermates and then (RS)-3,5-dihydroxyphenylglycine (DHPG)-induced protein synthesis was compared between wild type (WT) and FXS littermates. DHPG is a group I mGluR agonist that is of particular interest because it induces chemical long-term depression (LTD), which has shown to be aberrant in FXS model mice and is the foundation of the mGluR theory of FXS. This unique approach of studying both basal and DHPG-dependent protein synthesis allows for a unique pool of information, including the comparison of two different neuronal activity states. We used categorization metric (called a consistency filter) and gene ontology analysis (from DAVID (david.ncifcrf.gov/)) to determine the proteins that are changed reliably between genotypes at the basal level, and compared measured proteins between WT and FXS groups with and without DHPG to establish a set of candidate proteins in the mouse brain. There is minimal overlap between the de novo candidate proteins translated in basal and DHPG conditions in FXS mice and this strongly suggests that treating only the mGluR-induced translation would not fully correct changes in protein synthesis or protein expression aberrance. These data may therefore explain some of the limitations of targeting mGluRs in patients.

It is important to identify markers that are relevant in blood because as disclosed herein, it was observed that potential markers in relevant tissues like the brain are not always correlative with their status in blood. Thus, the candidates that are different between patients and control subjects in blood cannot be predicted from brain, nor can the direction of their dysregulation. mGlur5 and Grin2b are examples of such dichotomy. mGluR5 is a canonical candidate for FXS that has repeatedly shown to be elevated in FXS mouse and patients brains compared to control subjects and has been implicated in functional pathology (Lohith et al, 2013 Molec Autism, May 24; 4(1):15. doi: 10.1186/2040-2392-4-15, Dolen and Bear, 2008 J Physiol, March 15; 586(6):1503-8. doi: 10.1113/jphysiol.2008.150722; Ronesi et al, 2012, Nat Neuro, January 22; 15(3):431-40, S1. doi: 10.1038/nn.3033), however, we observed that mGlur5 is not appreciably changed in patient plasma compared to healthy controls (FIG. 4D). In addition, Grin2b which has been implicated in numerous neurological disorders including Autism and FXS, is shown to be decreased in our screen in FXS mouse brains and in our validation (FIG. 3D). However there are some patients that appear to be similar to healthy controls, and others with elevated quantities of Grin2b in human plasma (FIG. 4G). We also demonstrate that proteins like cofilin and FMRP can be detected reliably in the blood. Other suitable proteins include Ras, hexokinase, ACO2, eIF2a, PAK, Syngap, DBI. Therefore, a systematic analysis can be carried out to determine which candidates in the brain will be reproducible in the blood (or may have a subpopulation) and one cannot assume from literature, previous other studies that a marker will work in both brain and blood. Similarly, one cannot solely look at changes in the blood and assume a correlation with relevant brain activity, as they are distinct tissues with their own cellular processes and regulation. Therefore, having a screen that starts in the relevant tissue (the brain) and then a systematic process to evaluate candidates that may be present in peripheral tissues for active monitoring is useful.

Figure 2:
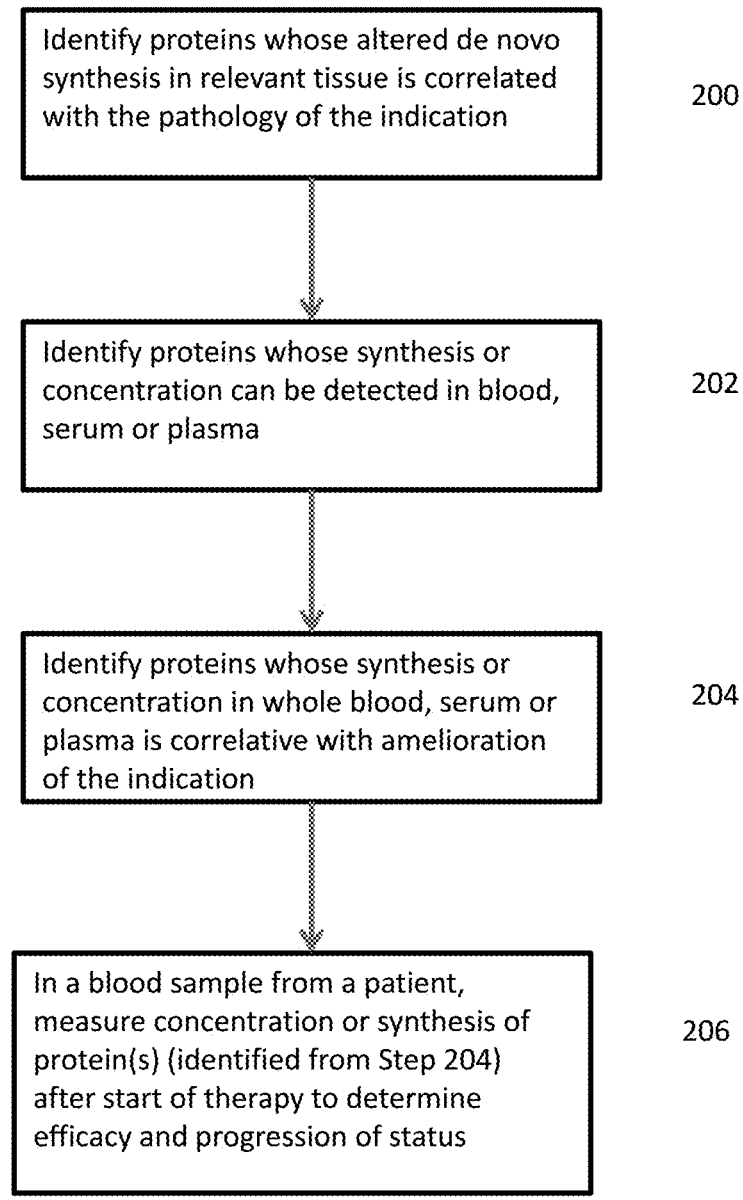
FIG. 2. Flow chart representing a method for identifying a protein whose status in blood can be used to monitor efficacy of treatment protocols.

In an embodiment of this disclosure, the method can be used as companion diagnostics to monitor efficacy of therapeutics. The method is illustrated in FIG. 2. In Step 200, proteins are identified whose altered de novo synthesis or level in relevant tissue or organ is correlative with the pathology of the indication. de novo protein synthesis determination in tissues can be carried out as described above. In Step 202, proteins are identified whose de novo synthesis can be detected in blood, plasma, serum or a fraction or portion thereof. de novo protein synthesis in whole blood, plasma, serum or sub-fractions of any of these can be carried out as described herein. In Step 204, proteins are identified whose level or de novo synthesis or other status in whole blood, plasma, serum or sub-fractions of any of these is correlative with a change in status (e.g., amelioration or progression) of the pathological state or indication. In Step 206 (representing the testing of patient samples), blood samples can be obtained from patients and concentration, de novo synthesis or other status of the proteins identified in Step 204 (or any other step) can be used to monitor efficacy of therapy or to monitor status of an individual. Each step described in the method of FIG. 1 or 2 is independent of the other steps. These steps may be carried out sequentially or in parallel. For example, Step 206 can be carried out independent of the other steps. Once proteins markers have been identified whose concentration, de novo protein synthesis or other status is correlative with amelioration or progression of an indication, patient blood samples or fractions or portions thereof can be tested as a function of time (with or without therapy). The term "therapy" as used herein is not restricted to administration of therapeutic agents, but includes surgical, radiological and other interventional approaches, and non-interventional approaches such as environmental, behavioral, psychiatric or other treatment approaches.

Figure 3:
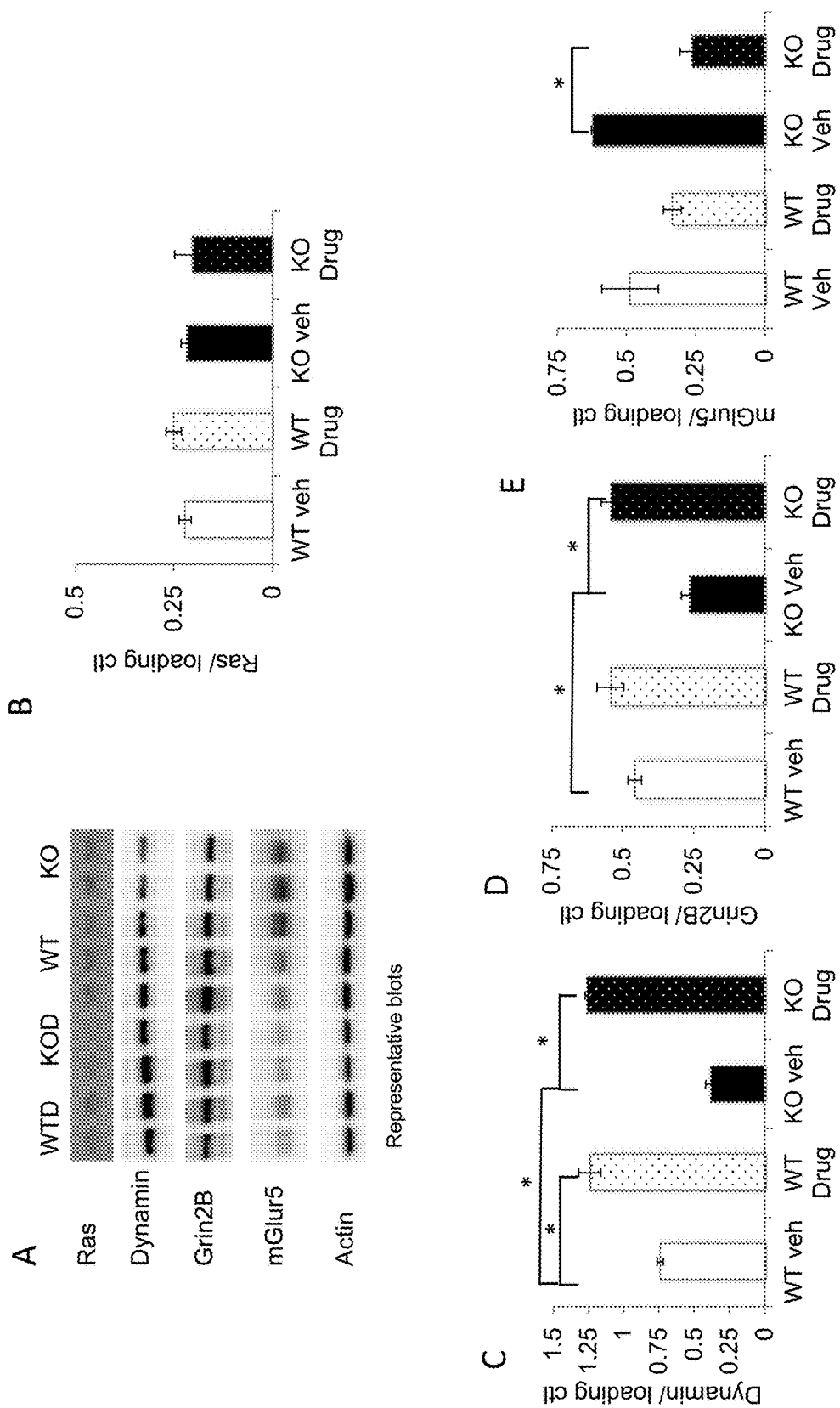
FIG. 3. Treatment with Ribosomal protein S6 kinase beta-1 (S6K1) inhibitor (S6K1i) (PF-4708671) drug that alleviates behavioral abnormalities in FXS model mice also rescues expression of 3 protein candidates in brain. This is presented as an example of deploying this method to find candidates that predict treatment outcome with a candidate drug/agent. A. Representative blot images from brains harvest from Fmr1 KO (FXS) and WT littermates that were treated chronically with a S6Ki drug. B-E. Quantification of relative concentration of 3 out of 4 candidates predicted to be altered by mass spec (Table 1) that respond show a treatment response.

The steps of this method are important because one cannot assume that just because global or organ-specific protein synthesis is rescued by a drug that a target disrupted by aberrant protein synthesis is rescued as well. For example, in FXS mice, Ras activity has been previously shown to be rescued in the brains of FXS mice by treatment paradigms (lovastatin) that also rescues general protein synthesis (Osterweil et al, 2013 Neuron, January 23; 77(2): 243-50. doi: 10.1016), however, as shown in FIG. 3 herein, it does not change with a S6K1 inhibitor which also affects general protein synthesis in the brain of FXS mice (Bhattacharya et al, 2016, Neuropsychopharmacology, July; 41(8):1991-2000. doi: 10.1038). Yes, surprisingly, as described herein, Ras levels in blood are correlative of effectiveness of treatment.

In one embodiment, the present disclosure provides one or more proteins whose level or de novo protein synthesis in blood can be used for patient stratification and or monitoring the progression of the disease in individual patients or monitoring efficacy of therapeutic approaches.

The levels or de novo synthesis of proteins that are found to be detectable in blood and which are correlative of the status of the pathology or indication, or which are reflective of their status in relevant tissues or organs can be determined and compared to a reference value or set of values to obtain the status of the pathology in the individual. Monitoring of protein levels or their de novo synthesis levels can be carried out over time in response to therapeutic approaches to determine the efficacy of the therapy.

An example of the steps of a method for identifying markers is provided in FIG. 9. As will be appreciated, the steps need not be run sequentially and can be run in parallel, where appropriate. Two or more steps may be combined. One or more steps may be skipped.

An example of steps involved for use in companion diagnostics is provided in FIG. 10. The steps need not be run sequentially and can be run in parallel, where appropriate. Two or more steps may be combined. One or more steps may be skipped.

The present disclosure provides a method for stratification of patients into subpopulations based on de novo protein synthesis in blood or concentration in blood of selected markers. The markers may be identified as being correlative with the status of a pathological condition in the relevant tissue. Subpopulations may be correlative of disease state, severity, disease progression or efficacy of treatment. For example, in the case of FXS, relationships of the subpopulations may be evaluated with respect to intelligence quotient (IQ), CGG repeat number, sex, age, drugs usage, perseverance score and additional autism diagnosis indicators. Based on designation of an individual to a subgroup, the most appropriate treatment may be identified, or the efficacy of a treatment may be determined, and based upon the status of the efficacy, the treatment may be continued, increased, decreased, reduced, supplemented, or terminated.

In one embodiment, the disclosure provides a method for patient stratification of individuals afflicted with Fragile X syndrome (FXS) comprising determining in a plurality of biological samples (e.g., blood, plasma or serum) obtained from individuals afflicted with FXS, de novo protein synthesis or levels of a protein selected from the group consisting of Ras, mGlur5, Grin2b, cofilin, FMRP, hexokinase, ACO2, eIF2a, PAK, Syngap, DBI, and combinations thereof; identifying if any difference in the de novo protein synthesis or levels are observed for one or more of the proteins compared to reference levels or synthesis; if differences are observed, then stratifying the individuals into subpopulations thereby distinguishing patient groups based on the levels or de novo synthesis of markers. The stratified subpopulations may then be correlated with IQ, CGG repeat number, sex, age, drugs usage, perseverance score or additional autism diagnosis indicators. The subpopulations may also be correlated with status of the pathology of the indication thereby allowing for monitoring of efficacy of treatment, or recurrence.

The disclosure further provides a method of treatment of an individual by monitoring the efficacy of the treatment regimen by evaluating the de novo protein synthesis or concentration of specific markers in blood. For example, in one embodiment, a change in blood levels of one or more markers selected from the group Ras, mGlur5, Grin2b, cofilin, FMRP, hexokinase, ACO2, eIF2a, PAK, Syngap, DBI, and combinations thereof in response to treatment is determined. In one embodiment, an individual afflicted with FXS can be subjected to a treatment for FXS, one or more of the above markers can be monitored, and if a preselected change (correlated with amelioration of FXS) is observed in the one or more markers, then the FXS treatment can be continued. In a specific embodiment, the method comprises subjecting an individual afflicted with FXS to a first treatment for FXS, monitoring the level of Ras in the blood, plasma or serum, if a change (e.g., increase) in the level of Ras is observed after a suitable period of time (e.g., any time from 1 to 4 weeks, or before or after that), then further subjecting the individual to the first treatment, or alternatively, supplementing a first treatment with a second treatment to ameliorate the FXS symptoms. If there is no change in the levels of Ras or there is no increase in the blood levels of Ras, then terminating the first treatment. The first and the second treatment may independently comprise administration of therapeutic agents, surgical, radiological and other interventional approaches, and non-interventional approaches such as environmental, behavioral, psychiatric approaches. In one embodiment, the treatment comprises administration of an S6K1 inhibitor (e.g., PF-4708671, FS-115, combinations thereof, and others). The measurement of do novo synthesis of proteins or levels of markers may be carried out prior to initiation of treatment and at one or more times are initiation of treatment. The times and frequency of measurement can be determined by a health care worker. For example, after initiation of the treatment, measurements can be made within minutes and continued up to days or months into the treatment. Measurements can be continued after termination of the treatment.

In one embodiment, this disclosure provides a method for treatment of an individual afflicted with fragile X syndrome (FXS) comprising: subjecting an individual to a first treatment for FXS; measuring de novo protein synthesis or level of a protein in the blood, plasma or serum of the individual, said protein being selected from the group consisting of Ras, mGlur5, Grin2b, cofilin, FMRP, hexokinase, ACO2, eIF2a, PAK, Syngap, DBI.; and if a change is observed in the de novo protein synthesis or level of said protein, then continue subjecting the individual to the first treatment, or alternatively, additionally subjecting the individual to a second treatment in addition to the first treatment. If no change is observed, then the first treatment can be terminated or reducing, and optionally a second treatment can be started.

In one embodiment, this disclosure provides a method for monitoring the efficacy of treatment for fragile X syndrome or a related disorder comprising: obtaining blood samples from an individual prior to initiation of treatment and at one or more time points following start of treatment; determining status of one or more of the following markers mGLUR5, Grin2B, Ras, hexokinase, ACO2, eIF2a, and PAK in whole blood, plasma or serum or a subcellular fraction of the cells present in blood, plasma or serum. The method may further comprise comparing the status of the markers to a reference. The method may further compare modifying the treatment if the marker or markers is/are not approaching reference levels with treatment.

The markers can be detected by methods commonly known in the art, such as, for example, affinity binding assays, immunological based assays, including ELISA, Western blotting and like. Specific antibodies for detection of Grin2b, Ras, mGluR5, hexokinase, ACO2, eIF2a, PAK, Syngap, DBI are commercially available.

In one embodiment, the present disclosure provides a kit or a panel for detection of levels of one or more proteins in blood or a fraction thereof. In one embodiment, the kit or panel comprises reagents for the detection of at least two markers. For example, the kit or panel may comprise reagents for the detection of two proteins e.g., detection materials for a first protein whose de novo synthesis in blood or a fraction thereof is correlative with amelioration of an indication upon therapeutic treatment; and detection materials for a second protein whose de novo synthesis in blood or a fraction thereof is correlative with amelioration of the indication upon therapeutic treatment. The kit may include other reagents such as buffers, immunological reagents and the like.

As an example for the detection of FXS or related conditions, a kit or panel may include detection agents for detecting and measuring Grin2b, Ras, mGluR5, hexokinase, ACO2, eIF2a, PAK, Syngap, DBI etc. In other examples, the panel or kits may include detection agents for measuring at least two, at least three, at least four or more protein markers in blood, which have been identified to be correlative with their levels in relevant tissues or with the status of the pathology. The kits can also comprise internal positive controls, buffers and the like. For example, in one embodiment, the disclosure provides a panel of two or more antibodies for the detection of protein markers, which markers are indicative of the status of fragile X syndrome, wherein each antibody is specific for mGLUR5, Grin2B, Ras, hexokinase, ACO2, eIF2a, PAK, Syngap, or DBI.

The present method represents a potential solution to the outcome measure problem of previous clinical trials in which there are no known or clear clinical markers to follow—such as neuropsychiatric, learning or behavioral disorders. The methods and compositions of the present disclosure are applicable to humans and non-human animals.

The following examples are provided for illustrative purposes and are not intended to be limiting.

Example 1

This example describes identification of protein markers whose concentration in blood can be used to determine status of FXS. Protein candidates known to be altered in the brain in fragile X syndrome (FXS) were evaluated to determine if they could serve as panel proteins for a blood based test. We first determined if any of these candidates could respond to amelioration of indication e.g., any drug treatments currently being explored for FXS. An animal model (FXS mice) was used to address this question. An S6K1 inhibitor was selected that has been shown to ameliorate behavioral, synaptic and protein synthesis deficits in FXS mice and human fibroblast lines (Bhattacharya et al, 2016, Kumari & Bhattacharya et al, 2014). The results are summarized in Table 1 below.

PF-4708671 was obtained from Sigma, Mo., USA. Littermate matched mice underwent 10 days of daily 25 mg/kg intraperitoneal injections of PF-4708671 in a vehicle consisting of saline +5% v/v of Tween-80 (Sigma). On day 10, 90 mins after the final injection mice were killed by cervical dislocation and the hippocampus was quickly dissected to yield whole hippocampal lysates. Simultaneously, trunk blood also was collected to monitor peripheral levels of proteins.

TABLE 1

Summary of data where FXS model mice were treated with two S6K1 inhibitors (S6K1i) and examined for improvements in protein synthesis, behavior and spine morphology. The inhibitors used were PF-4708671 and FS-115.

| Phenotype | Rescued by S6K1i |
| --- | --- |
| Increased protein synthesis | Both inhibitors rescued |
| Increased marble burying behavior | One inhibitor rescued |
| Aberrant social novelty behavior | Both inhibitors rescued |
| Aberrant y-maze reversal learning | Both inhibitors rescued |
| Aberrant spine morphology | Both inhibitors rescued |

We examined 4 candidates (Ras, dynamin, Grin2B, and mGlur5) in the brains of FXS and WT littermates following chronic treatment with the S6K1 inhibitor and note 3 out of 4 are statistically improved in FXS model mice following treatment, with the fourth protein being upstream and part of a different regulatory pathway (FIG. 3). Thus, the candidates correlate with improved behavior in the brain. We therefore evaluated if they could be measured and quantified in a peripheral tissue such as blood. Animals were treated as described above with PF-4708671, then animals were euthanized via cervical dislocation and brain tissue was collected on ice and snap frozen. Lysates were then prepared as previously described (Bhattacharya et al, 2016, incorporated herein by reference) and analyzed by western blot.

Figure 4:
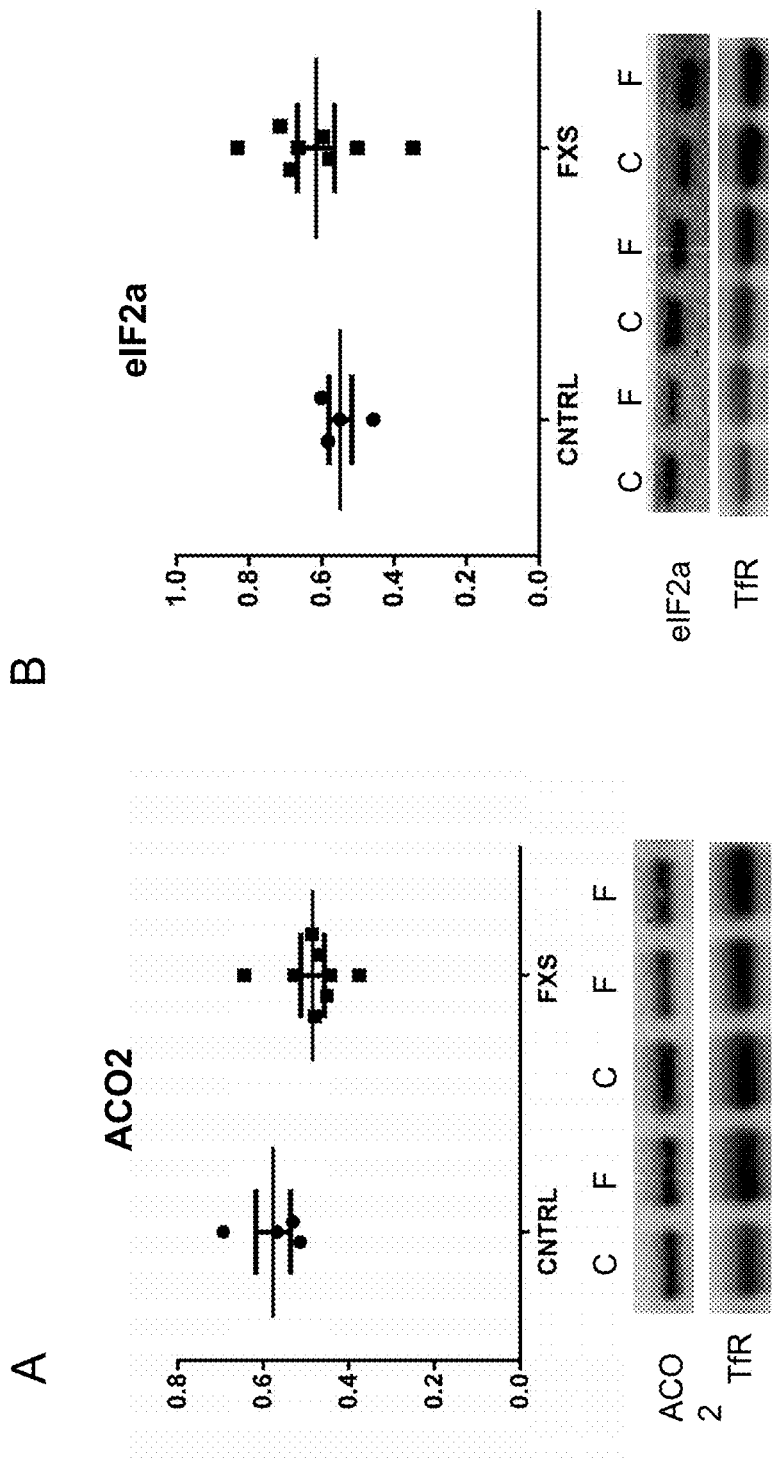
FIG. 4. Quantification of 7 protein candidates in human patient plasma in a pilot study. (A): ACO2; (B): eIF2a; (C): Hexokinase; (D): mGLUR5; (E): PAK; (F): RAS; (G): Grin2B. Candidates were selected by using the present screen and validated by Western blot in FXS human patient plasma versus control human samples. Many candidates demonstrated divergence between FXS and control subjects, with some candidates showing potential subpopulations that differed from controls.
Figure 4:
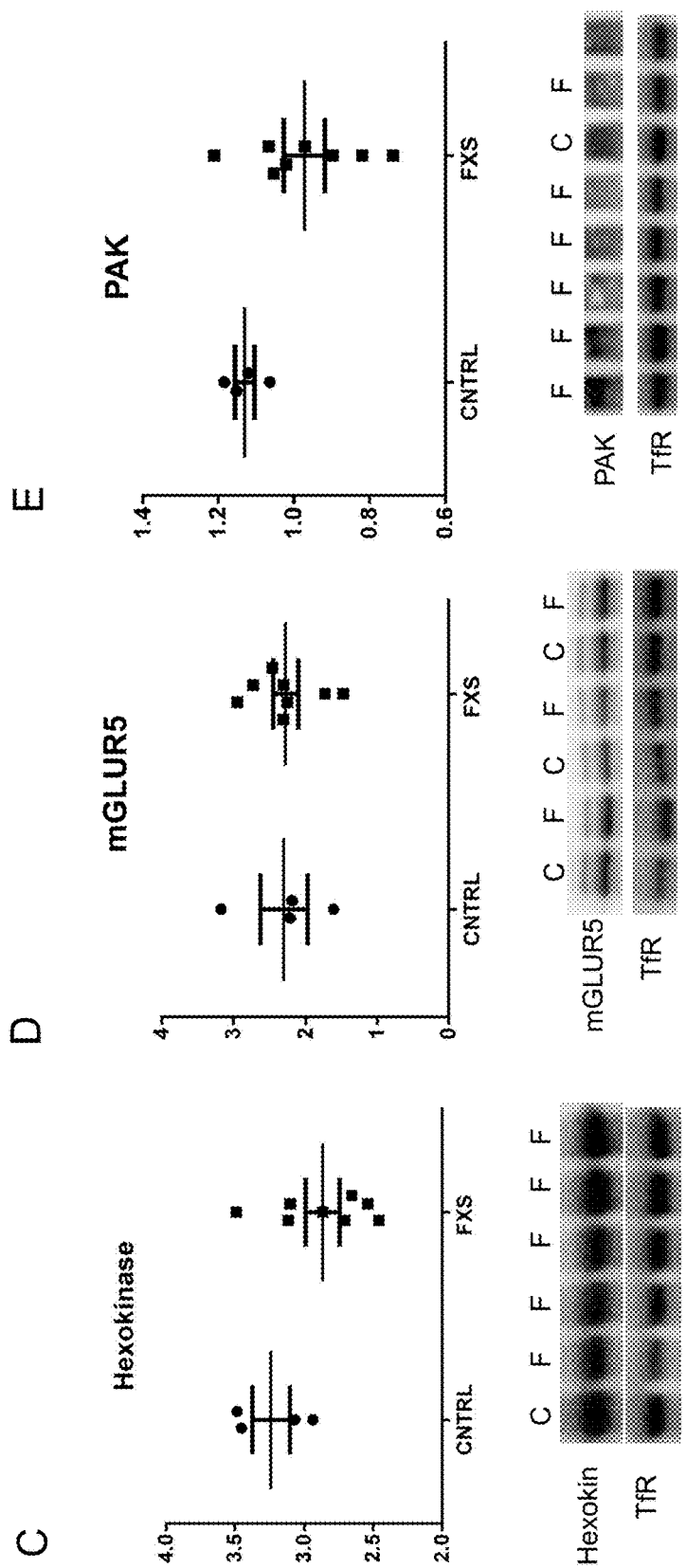
Figure 4:
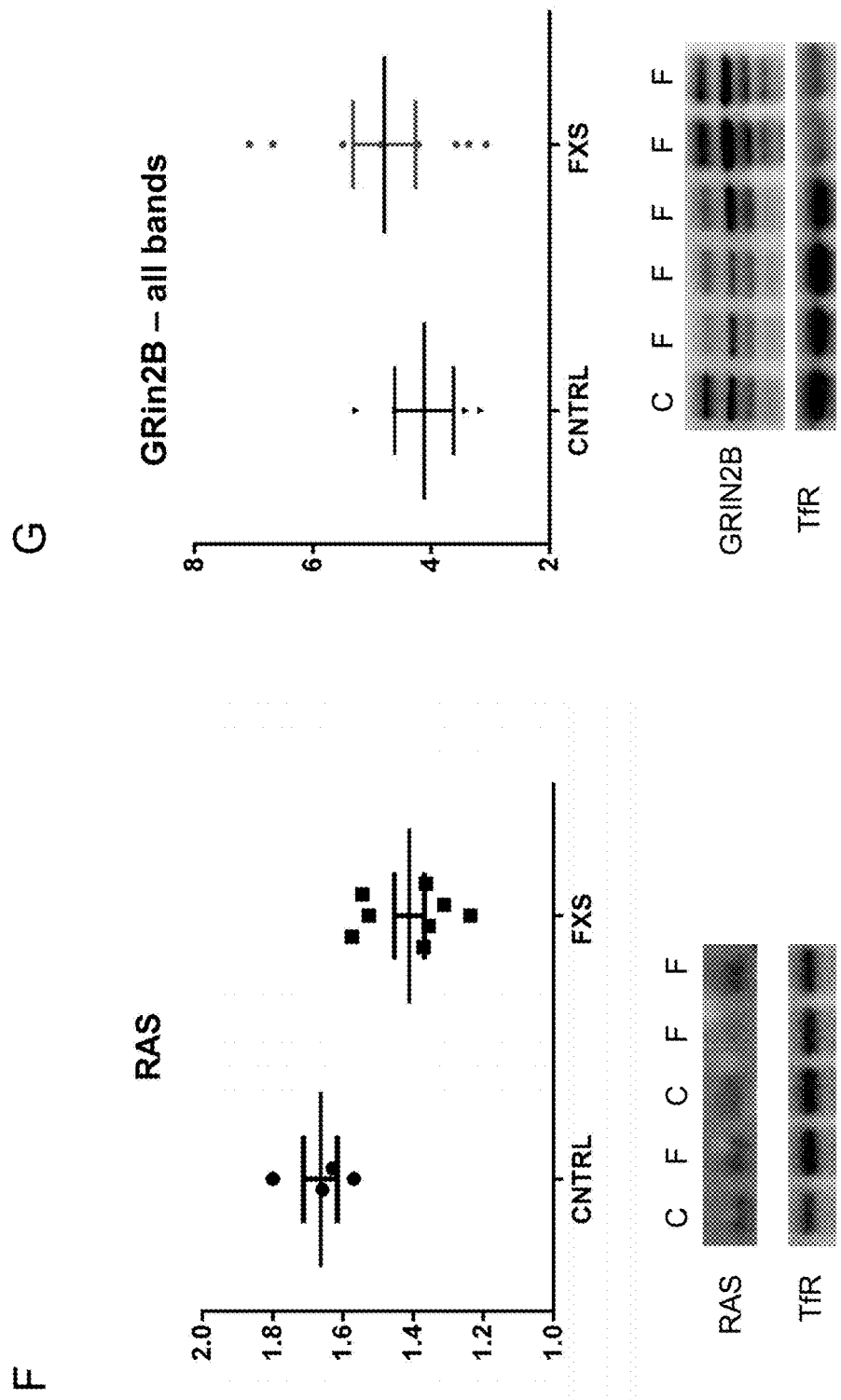

We generated a list of candidates that would be relevant outside the brain in peripheral tissues and which proteins were reported to be expressed in blood. We started with a list of proteins to identify which proteins could be detected in blood using western blot (Table 2, FIG. 5). Of these, some, such as cofilin could not be identified in blood and other, such as FMRP, had different expression patterns than in the brain. We were able to identify 7 proteins in the first round that were expressed in mouse blood and selected these for testing in the human pilot study. Both serum and plasma had detectable candidate proteins, however, plasma was more readily available, so more of those samples were processed. We could easily visualize 7 proteins by western blot, however, only 5 of them differed in part (subpopulation of patients) or wholly (all patients tested) from the control group (FIG. 4). Interestingly, one of the targets that did not differ between the two groups in blood was mGlur5 suggesting that it would not be an ideal candidate as a peripheral marker even though it is altered in the brain. These data provide strong evidence that the candidate markers we have identified are both relevant to FXS and that are capable of differentiating both FXS patients from control patients and may be able to stratify subgroups of FXS patient populations for better groupings and analysis of future clinical trials.

Methods:

Candidate list was derived from 3 independent proteomic screens. A cohort of 9 mice (wild type and FXS litter mates) were used for each proteomic screen. Briefly we isolated hippocampal slices from each mouse brain and incubated it in artificial cerebrospinal fluid (ACSF) for 65 mins to recover them from tissue trauma and injury of slice preparation. We then incubated the slices with 1 mM AHA and 40 uM SILAC tags (heavy or medium isotopic labelled arginine or lysine) for 4 hours at 32° C. to label all de novo synthesized proteins within this time window. For basal screen this labeling was carried out for another hour, while for the DHPG (activity dependent) screen we stimulated slices with 100 micromolar (uM) DHPG for 15 mins followed by complete drug washout and chased in AHA and SILAC for another 1 hour. Slices were then snap frozen for further processing.

Slices were lysed in slices were lysed in buffer containing 8 M urea, 200 mM Tris pH 8, 4% CHAPS, 1 M NaCl, and protease inhibitor cocktail. Lysates of the WT and FXS were combined now for the basal screen, WT with and without DHPG and FXS with and without DHPG for the activity dependent screens, all in equal volume. The mixed lysate was sonicated to reduce viscosity. AHA labeled nascent proteins were covalently coupled to alkyne agarose beads using reagents provided in a protein enrichment kit (Thermo Fisher Scientific). Proteins-beads complex were then alkylated with iodoacetamide at room temperature. The proteins were washed thoroughly with multiple buffers changes of SDS wash buffer, 8 M urea, and 20% acetonitrile. Protein bead complex were digested with trypsin on-resin at 37° C. overnight in 25 mM ammonium bicarbonate and the resulting tryptic peptides were desalted and dried under vacuum. Samples so prepared were then taken to mass spectrometric analyses.

For LC-MS, a mass spectrometer was used. A self-packed 75-μm×25-cm reverse phase column (Reprosil C18, 3 μm) was used for peptide separation. Peptides were eluted by a gradient of 3-30% acetonitrile in 0.1% formic acid over 120 min (for the slice samples) a flow rate of 250 nL/min at 45° C. The mass spec was operated with survey scans acquired at a resolution of 50,000 at m/z 400 (transient time=256 ms). Up to the top 10 most abundant precursors from the survey scan were selected with an isolation window of 1.6 Thomsons and fragmented by higher-energy collisional dissociation with normalized collision energies of 27. The maximum ion injection times for the survey scan and the MS/MS scans were 60 ms, respectively, and the ion target value for both scan modes were set to 1,000,000. Peptide traces so detected where then funneled to the next step of protein Identification and Quantitation.

To summarize the above, de novo peptides contained 2 labels, one AHA and one SILAC labelled arginine and lysine. The samples were first enriched using AHA and then differences in protein concentration was measured using mass spectroscopy.

The raw files were processed using a computational proteomics platform (MaxQuant version 1.2.7.0) for peptide identification and quantitation. The fragmentation spectra were searched against the Uniprot mouse (for brain samples) protein database, allowing up to two missed tryptic cleavages. Carbamidomethylation of cysteine was set as a fixed modification, and oxidation of methionine and protein N-terminal acetylation, D4-lysine, 13C6-arginine, 13C6-15N2-lysine and 13C6-15N4-arginine were used as variable modifications for the database search. The precursor and fragment mass tolerances were set to 7 and 20 ppm, respectively. Both peptide and protein identifications were filtered at 1% false discovery rate (FDR).

Raw files were processed using the MaxQuant software package (v. 1.2.7.0) with the default parameters, including static modifications (carbamidomethylation at cysteine), and a minimum ratio count of 2. Proteins were identified using the tools FASTA and UNIPROT. MaxQuant normalized H/M ratios (heavy vs. medium isotopes) were used for quantitative analysis. Ratios were inversed for experiments with reversed isotopic labeling. Total intensities were calculated as the sum of the heavy and medium ion intensities, as reported by MaxQuant. The statistical significance of the log-2 transformed ratios and total intensities was analyzed by the Perseus software (v.1.1.1.34) using the Significance_B option and the Benjamini-Hochberg correction to account for multiple hypothesis testing. Proteins with p≤0.3 were selected and then scored for consistency. Only those proteins measured at least twice and those that were consistently up or down regulated each time they were detected were selected. Only those proteins that met all these criteria were deemed candidates. For each Mass spec run we got three candidate list.

To choose the next level of candidates we compared the 3 lists and subjected them to gene ontology. We were interested in functions like synaptic transmission, metabolism, actin rearrangement etc. Gene Ontology analysis was performed using the Database for Annotation, Visualization and Integrated Discovery (DAVID, Huang et al., 2009, Nature Protocols, 4(1):44-57). The background was considered as all proteins measured in hippocampal brain slices (Table S2). Clusters with enrichment scores over 1.3 with FDR values of less than 0.05 were considered, with the most focus given to candidates that appeared multiple times in clusters that met this criteria.

From the brain mass spec we got a list of 324 candidates that whose concentration was reliably altered. We then introduced two additional qualitative filters to find those that would be eligible to be used as biomarkers in the blood: 1) the protein needs to be ubiquitously expressed in blood and brain, b) protein should be within detectable size range—too large proteins upwards of 300 kDa or lesser than 20 kDa are extremely hard to probe for with biochemical tests, c) protein should have been included in GO categories, d) available reliable antibodies found and d) demonstrated role in brain function in FXS, autism or any other neurological disease.

Details of de novo protein synthesis method for hippocampal slices are also provided in Bowling et al., 2016, Neuropharmacology, January; 100:76-89, incorporated herein by reference.

Brain tissues were obtained immediately following euthanasia, snap frozen and homogenized in lysis buffer containing protease and phosphatase inhibitors. Lysates were then analyzed using Western blotting and the levels of specific candidates was determined using densitometry and comparing them to a known loading control such as actin, Gapdh or transferrin receptor.

Example 2

Figure 6:
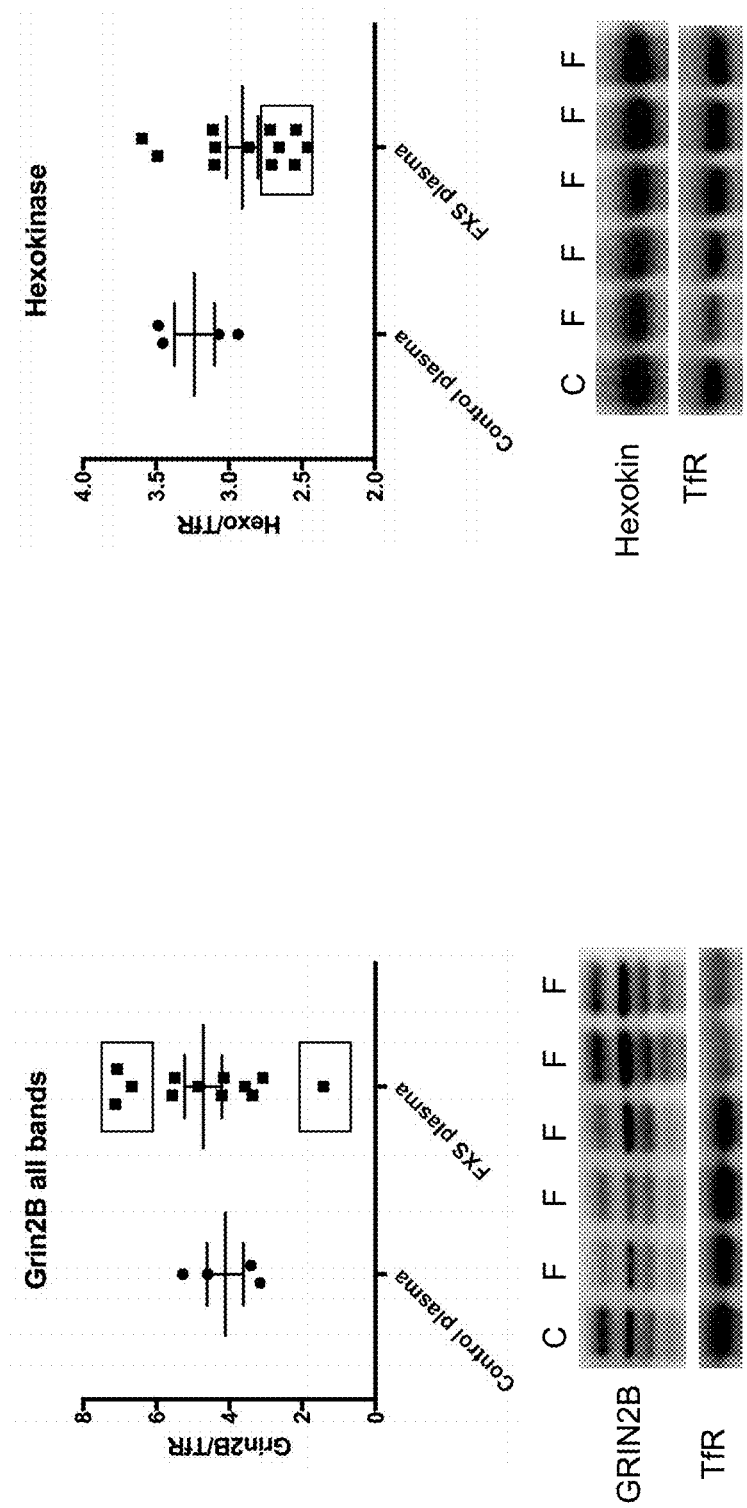
FIG. 6. Quantification of protein candidates in human patient plasma. Data on 2 candidate proteins, Grin2B and Hexokinase using a larger sample than in FIG. 4. Subpopulations that could be used to detect subgroups for patient stratification are shown in boxes.

This example describes data using increased number of patient samples. As described in Example 1, candidate markers were selected using the screening method described herein and validated by Western blot in FXS human patient plasma versus control human samples. Many candidates demonstrated divergence between FXS and control subjects. FIG. 6 provides data on two candidates and shows evidence of potential subpopulations that could be used to detect subgroups for patient stratification (in boxes). The data confirms subgroups of protein expression in Fragile X patient plasma. Because these results were seen in an increased numbers of Fragile X patients, this underscores likelihood of patient subgroups in human plasma in candidate proteins.

Figure 7:
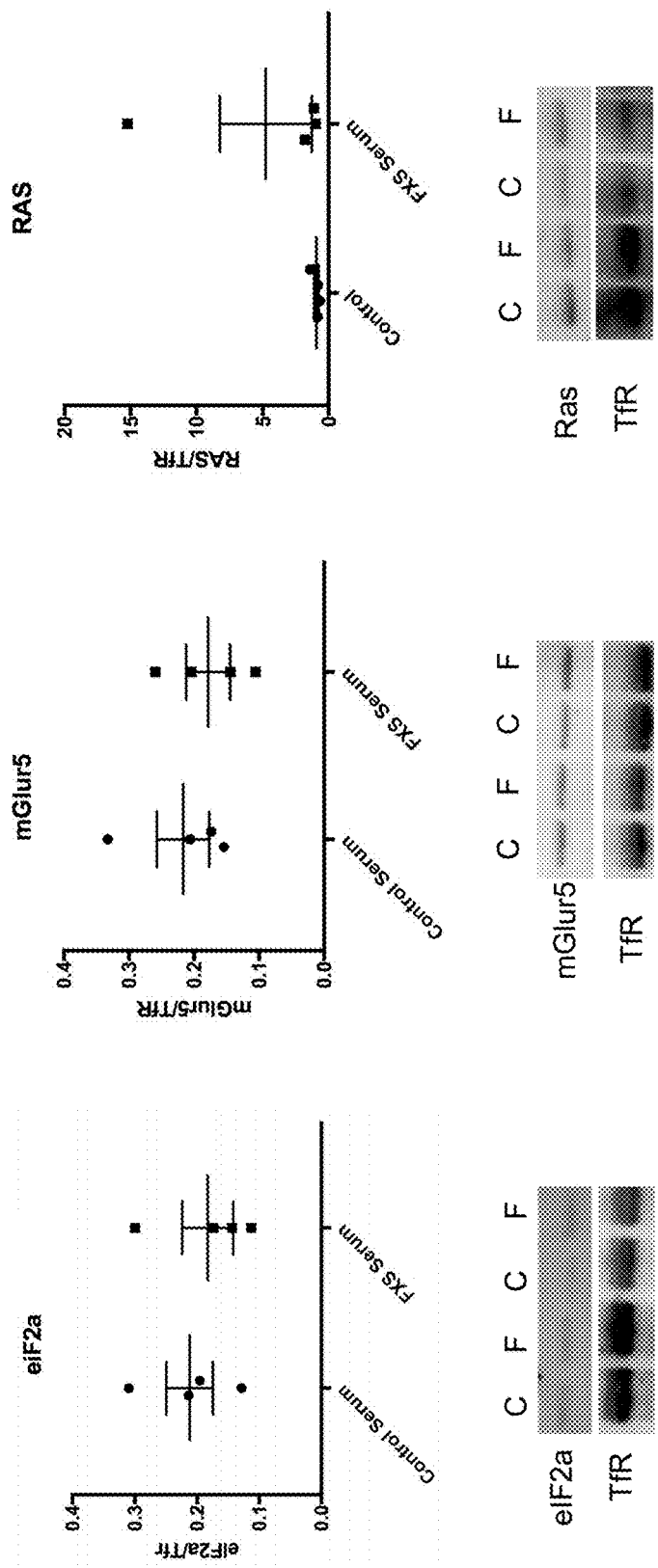
FIG. 7. Candidate proteins can also be detected in serum. Candidates were selected from the present screen and validated by Western blot in FXS human patient serum versus control human samples. Some candidates demonstrated divergence between FXS and control subjects. One example (RAS) shows clear evidence of potential subpopulations that could be used to detect subgroups for patient stratification—the average of RAS outside the patient at 15 is higher than control as well (1.3 for patient vs. 0.9 for control).

Protein expression changes in candidate proteins can also be measured in human serum (not just plasma). As shown in FIG. 7, some proteins show subpopulations (such as Ras). Further, it is noteworthy that while Ras showed a decrease in the plasma (FIG. 4F), it appears to be elevated in serum. This may be due to preparation differences as clotting requires GTPase activity. In addition, mGlur5 is mainly similar between Control and FXS, however there was one patient in which the level was lower. Thus, these markers can be measured in both serum and plasma.

Example 3

Figure 8:
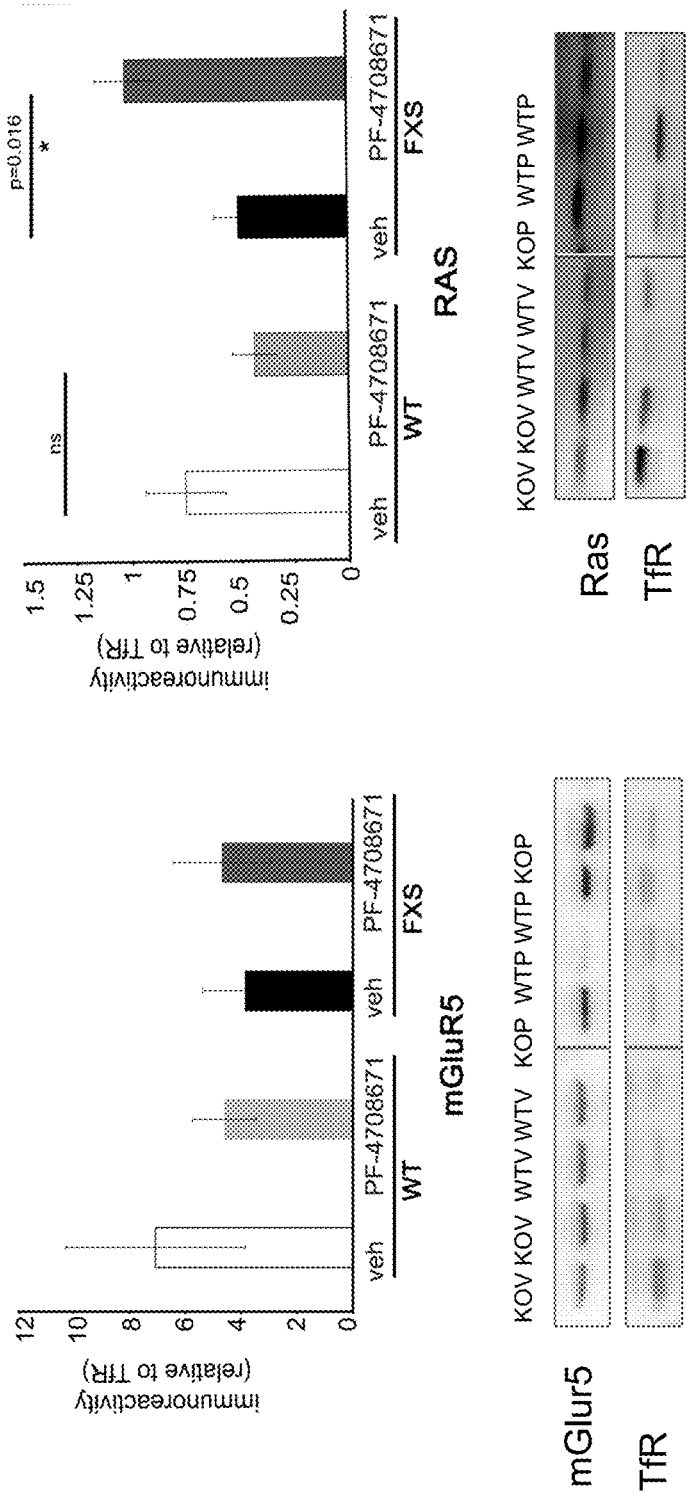
FIG. 8. Blood profiles of candidates similar in FXS model mice as they were in humans and one is rescued by a p70 S6 Kinase 1 inhibitor (S6K1 inhibitor) treatment. Concentration levels of mGluR (D) and Ras (E) in mouse trunk blood treated with vehicle or PF-4708671 (S6K1i) for 10 days. N=3 animals per treatment per genotype. Cut images for the same protein are from the same blot and same exposure.

This example demonstrates that markers in blood can be used to monitor treatment of FXS. FXS or wild type mice were treated with an S6K1 inhibitor, PF-4708671 (S6Ki) for 10 days. Concentration levels of the two markers—mGluR and Ras in mouse trunk blood treated with vehicle or the S6Ki were determined. N=3 animals per treatment per genotype were used. Statistical analyses was done using two-way ANOVA (genotype×treatment). Results are shown in FIG. 8. P=0.0079 for interaction and p=0.019 for FXS±S6Ki and p=0.16 for WT±S6Ki.

The average values (+/−SD) were: WT vehicle (veh): 0.91±0.19; WT±S6Ki: 0.62±0.20 (less 32% from WT veh); FXS±veh: 0.67±0.19 (less 26% from WT veh); FXS+veh: 1.19±0.21 (31% greater that WT veh). Thus, the effect of the drug is specific to FXS and appears to have an opposite effect in WT treated samples. A 2 way ANOVA to check the effect of the treatment and genotype condition shows a specifically significant result for FXS±S6Ki to be 0.0007. This shows the change in Ras levels is unique to the FXS state and hence can be used as a Biomarker. Within groups the p values were: WT veh vs FXS Veh: p=0.17; WT veh vs WT S6Ki: p=0.09; FXS veh vs FXS S6Ki: p=0.009; and FXS S6Ki vs WT S6Ki: p=0.005.

Thus, while two candidates showed similar profiles in FXS model mouse blood to human patients, one was rescued with S6K1 inhibitor and can therefore be used to monitor efficacy of treatment of FXS patients. This is because treatment with S6K1 inhibitor rescues levels of some candidate proteins in the blood as well, not just the brain.

While the invention has been described through various embodiments and examples, these descriptions are intended to be illustrative. Routine modifications will be apparent to those skilled in the art, which modifications are intended to be included in the present disclosure.

What is claimed is:

1. A panel consisting of antibodies for the detection of protein markers metabotropic glutamate receptor 5 (mGLUR5), glutamate ionotropic receptor NMDA type subunit 2B (Grin2B), Ras, hexokinase, aconitase 2 (ACO2), eukaryotic translation initiation factor 2a (eIF2a), serine-threonine protein kinase (PAK), synaptic Ras GTPase-activating protein 1 (Syngap), and acyl-CoA-binding protein (DBI), which markers are indicative of the status of fragile X syndrome, each said antibody being specific for mGLUR5, Grin2B, Ras, hexokinase, ACO2, eIF2a, PAK, Syngap, or DBI.

2. A panel consisting of antibodies for the detection of protein markers aconitase 2 (ACO2), Ras, hexokinase, and metabotropic glutamate receptor 5 (mGLUR5) and glutamate ionotropic receptor NMDA type subunit 2B (Grin2B), which markers are indicative of the status of fragile X syndrome, each said antibody being specific for ACO2, Ras, hexokinase, Grin2B, or mGLUR5.

3. A panel consisting of antibodies for the detection of protein markers aconitase 2 (ACO2), Ras, and hexokinase, which markers are indicative of the status of fragile X syndrome, each said antibody being specific for ACO2, Ras, or hexokinase.

4. A panel of antibodies consisting of antibodies for the detection of protein markers: i) aconitase 2 (ACO2), ii) Ras, iii) hexokinase, and iv) metabotropic glutamate receptor 5 (mGLUR5) or glutamate ionotropic receptor NMDA type subunit 2B (Grin2B); which markers are indicative of the status of fragile X syndrome, each said antibody being specific for ACO2, Ras, hexokinase, mGLUR5 or Grin2B.

* * * * *